(12) United States Patent
Howton et al.

(10) Patent No.: US 7,853,066 B2
(45) Date of Patent: Dec. 14, 2010

(54) ENDLESS BELT

(75) Inventors: Brian Howton, Walla Walla, WA (US); Ken Carambot, Milton Freewater, OR (US); Robert Reusch, Grand Rapids, MI (US)

(73) Assignee: Key Technology, Inc., Walla Walla, WA (US)

( * ) Notice: Subject to any disclaimer, the term of this patent is extended or adjusted under 35 U.S.C. 154(b) by 953 days.

(21) Appl. No.: 11/714,471

(22) Filed: Mar. 5, 2007

(65) Prior Publication Data

US 2008/0217140 A1 Sep. 11, 2008

(51) Int. Cl.
*G06K 9/00* (2006.01)

(52) U.S. Cl. ...................................................... 382/141

(58) Field of Classification Search ................. 382/132, 382/141–150; 348/86, 92, 125
See application file for complete search history.

(56) References Cited

U.S. PATENT DOCUMENTS

| | | | |
|---|---|---|---|
| 4,360,836 A | 11/1982 | Breck et al. | |
| 4,830,194 A | 5/1989 | Kajiura et al. | |
| 4,914,289 A | 4/1990 | Nguyen et al. | |
| 5,185,772 A | * | 2/1993 | Shirouzu et al. .............. 378/29 |
| 5,989,175 A | 11/1999 | Kawanishi | |
| 6,341,878 B1 | 1/2002 | Chiang | |
| 6,870,610 B1 | 3/2005 | Struckhoff et al. | |
| 6,914,678 B1 | 7/2005 | Ulrichsen et al. | |
| 2006/0102528 A1 | 5/2006 | Bourely | |

FOREIGN PATENT DOCUMENTS

WO WO 2005/106438 11/2005

OTHER PUBLICATIONS

PCT/US08/02575, Sep. 2, 2009, PCT International Prelim. Exam. Report.

* cited by examiner

*Primary Examiner*—Daniel G Mariam
(74) *Attorney, Agent, or Firm*—Wells St. John, P.S.

(57) ABSTRACT

An endless belt for an object inspection system is described and which includes a flexible foundation layer; and a substantially transparent layer juxtaposed upon the flexible foundation layer, and which supports an object to be inspected, and which reflects and refracts a source of electromagnetic radiation so as to irradiate the object to be inspected.

14 Claims, 3 Drawing Sheets

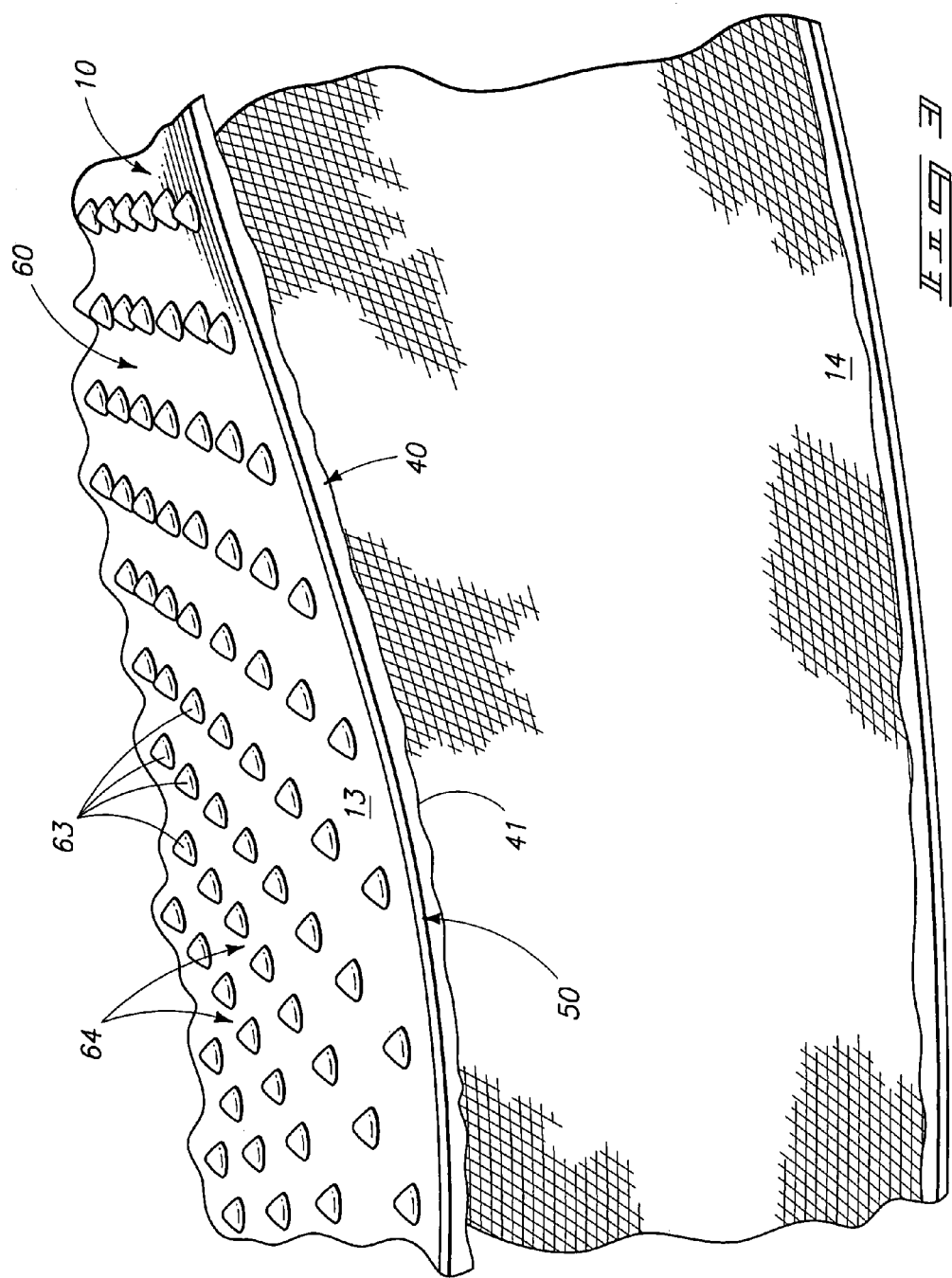

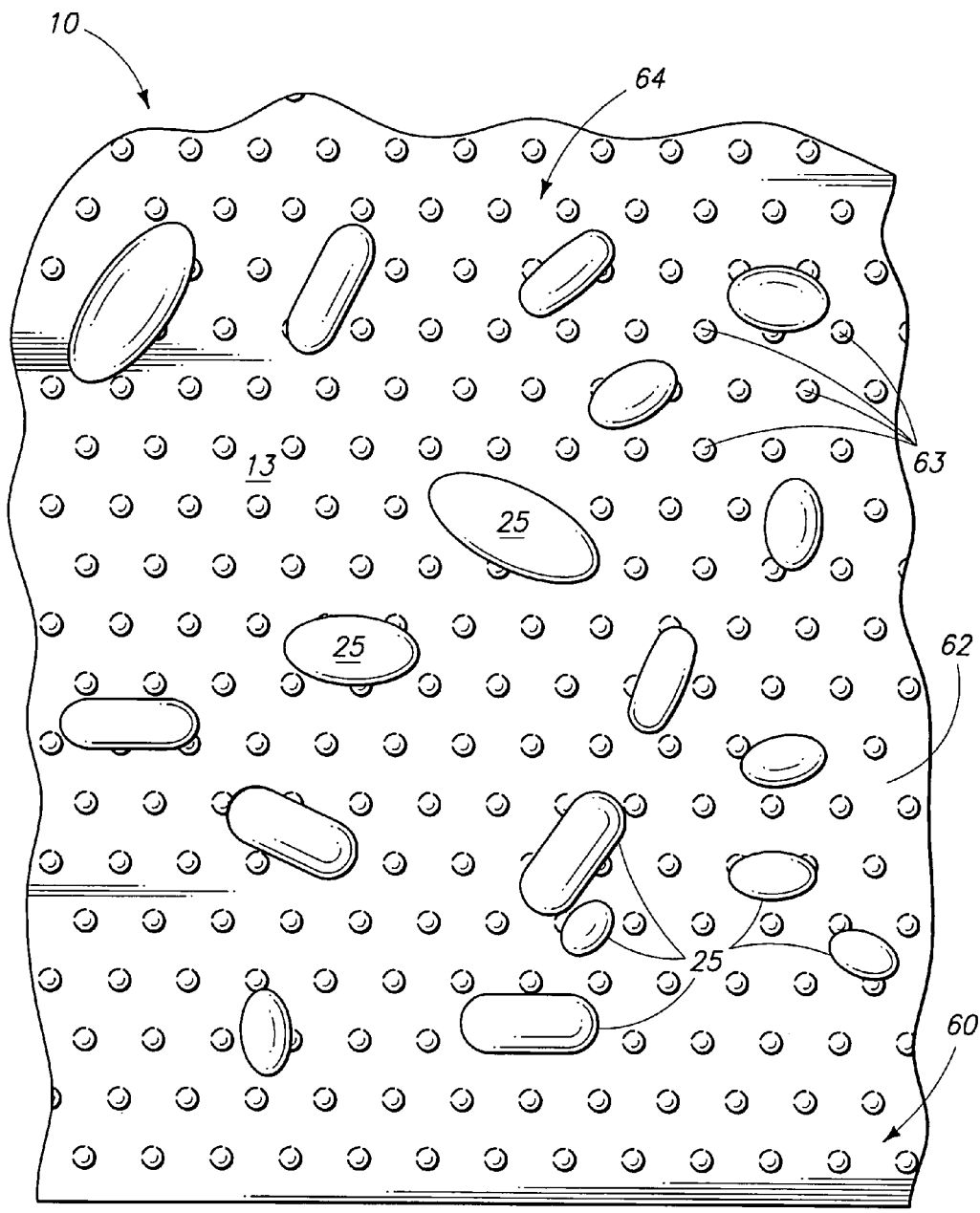

ENDLESS BELT

TECHNICAL FIELD

The present invention relates to an endless belt, and more specifically to an endless belt which finds usefulness when employed with an object inspection system and which supports an object to be inspected as it moves along a course of travel, and which further reflects and refracts a source of electromagnetic radiation so as to irradiate the object to be inspected.

BACKGROUND OF THE INVENTION

The beneficial effects of employing various methods and apparatus for illuminating an object of interest for purposes of inspection and the like are well known. The prior art is replete with numerous examples of prior art teachings which suggest various means for effectively illuminating an object of interest so as to prevent shadows, or further generating appropriate reflected light in given wavelengths which then may be processed by an image processor.

An example of a prior art reference similar to that described, above, is shown in U.S. Pat. No. 6,341,878 to Chiang. The teachings of that patent relate to a method and apparatus for providing uniform diffuse illumination to a surface. This prior art reference discloses in some detail the prior art practices relative to providing illumination of an object of interest. Referring now to FIG. 1 of that patent, it will be seen that an object to be inspected 44 is placed upon a supporting surface 12 which may be stationary or moving and wherein light 30 is reflected from a reflector 16 so as to illuminate the supporting surface thereof. Referring now to FIG. 2 of that same patent, a reflector 100 is provided, however, the object to be inspected is illuminated from below by means of a diffused light source 122. This diffused light is operable to reflect from an overhead parabolic reflector at various angles to provide the advantages as outlined in that patent.

While the prior art illumination methodology as provided herein has operated with some degree of success, various shortcomings are attendant with the practices associated with the prior art devices such as seen in U.S. Pat. No. 6,341,878. For example, one of the chief shortcomings associated with an assembly such as seen in that reference relates to the problems associated with the obscuring of the light which is passed through the diffuser as employed with that invention. Inasmuch as the diffuser assembly is positioned below the product to be inspected, debris or other material which finds its way onto the top of the diffuser has the effect of obscuring or otherwise blocking light passing through the underlying diffuser assembly so that the light which was to be reflected from the reflector does not reach the object to be inspected. Therefore, unless the prior art device is kept perfectly clean, some amount of light will not reach the object to be inspected thereby not thoroughly illuminating the product that is being inspected.

An endless belt that is useful in an object inspection system and which avoids the shortcomings attendant with the prior art practices utilized heretofore is the subject matter of the present application.

SUMMARY OF THE INVENTION

Therefore, a first aspect of the present invention relates to an endless belt for an object inspection system which includes a flexible foundation layer; and a substantially transparent layer juxtaposed upon the flexible foundation layer, and which supports an object to be inspected, and which reflects and refracts a source of electromagnetic radiation so as to irradiate the object to be inspected.

Another aspect of the present invention relates to an endless belt for an object inspection system which includes a flexible foundation layer; a contact layer having a first side, and an opposite second side, and which is fabricated from a substantially transparent material, and wherein the first side is juxtaposed relative to the flexible foundation layer, and wherein the contact layer supports an object to be inspected; and a source of electromagnetic radiation is directed at the endless belt, and which is partly reflected by the first side of the contact layer, and partly refracted by the substantially transparent material, and partly reflected by the second side of the contact layer so as to irradiate the object to be inspected; and wherein the second side of the contact layer has a surface topology which creates a coefficient of friction, and which inhibits the movement of the object to be inspected relative to the endless belt.

Still further, another aspect of the present invention relates to an endless belt for an object inspection system, and which includes a first foundation layer fabricated from a fabric and a resin; a second pigmented layer juxtaposed relative to the first layer; a third substantially transparent contact layer with a first side, and an opposite second side, and wherein the first side of the third layer is juxtaposed relative to the second layer, and wherein the second side of the third layer supports an object to be inspected, and which further defines a plurality of crowns and valleys within which the object to be inspected is positioned, and which further provides a coefficient of friction which inhibits the movement of the object to be inspected.

Yet another aspect of the present invention relates to an endless belt for an object inspection system which includes an opaque flexible foundation layer having an upwardly facing surface; an optically transparent layer deposited upon the upwardly facing surface of the flexible foundation layer, and which supports an object to be inspected; and a source of electromagnetic radiation positioned above the endless belt, and which, when energized, emits electromagnetic radiation which is directed onto the endless belt and the object to be inspected, and wherein the emitted electromagnetic radiation is passed, and reflected in part, by the optically transparent layer so as to substantially reduce any shadow created by the object to be inspected on the endless belt.

These and other aspects of the present invention will become more apparent hereinafter.

BRIEF DESCRIPTION OF THE DRAWINGS

Preferred embodiments of the invention are described below with reference to the following accompanying drawings.

FIG. 3 is a perspective, side-elevation view of a first and second course of an endless belt for an object inspection system of the present invention.

FIG. 4 is a top plan view of an endless belt for an object inspection system, and which shows the endless belt supporting various products to be inspected.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
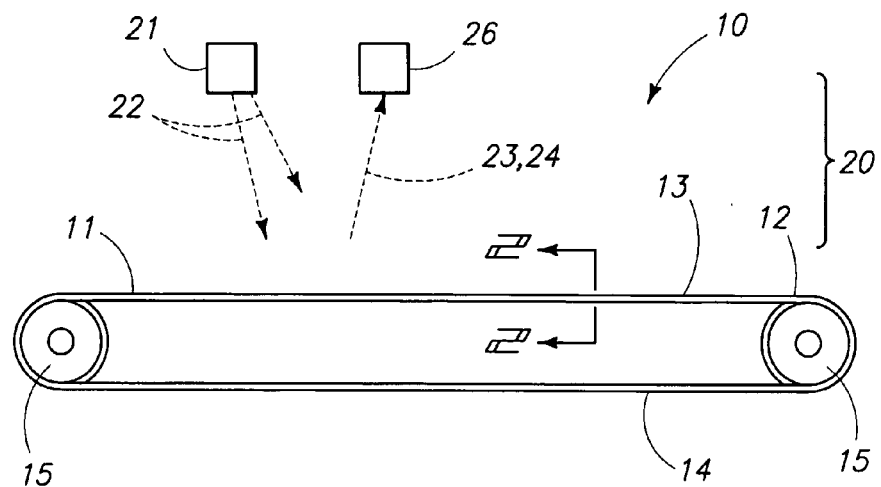
FIG. 1 is a greatly simplified schematic view of an object inspection system which incorporates the teachings of the present invention.

An endless belt for use in an object inspection system is generally indicated by the numeral 10 in FIG. 1. As seen therein, the endless belt 10 has a first end 11; an opposite second end 12; an upper course 13; and a lower course 14. The endless belt is driven and supported by opposite drive rollers which are generally indicated by the numeral 15.

As best understood by a study of FIG. 1, the endless belt 10 is useful when employed with an object inspection system 20, and which is generally depicted in FIG. 1. The object inspection system 20 typically includes a source of electromagnetic radiation 21 which is positioned above the upper course 13, and which, when energized, emits electromagnetic radiation 22 which is directed towards the upper course, and which is reflected 23, at least in part, and refracted 24 so as to irradiate an object to be inspected, and which is generally indicated by the numeral 25. As discussed herein, the object 25 to be inspected relates to various pharmaceutical products such as gel capsules, tablets and the like, some of which are seen in FIG. 4. As should be understood, some of the objects 25 to be inspected may include gelatin capsules which are somewhat translucent and which allow for the passage of visible electromagnetic radiation therethrough. The invention is not limited, however, to these products, alone, but could be used successfully with a number of different products. The object inspection system 20 also includes a camera which is generally indicated by the numeral 26, and which is operable to capture reflected or refracted light images 23/24 which come from the upper course 13 of the endless belt 10, and which later is supplied to an image processor (not shown) for further utilization in accordance with prior art teachings which are well known in the art.

Figure 2:
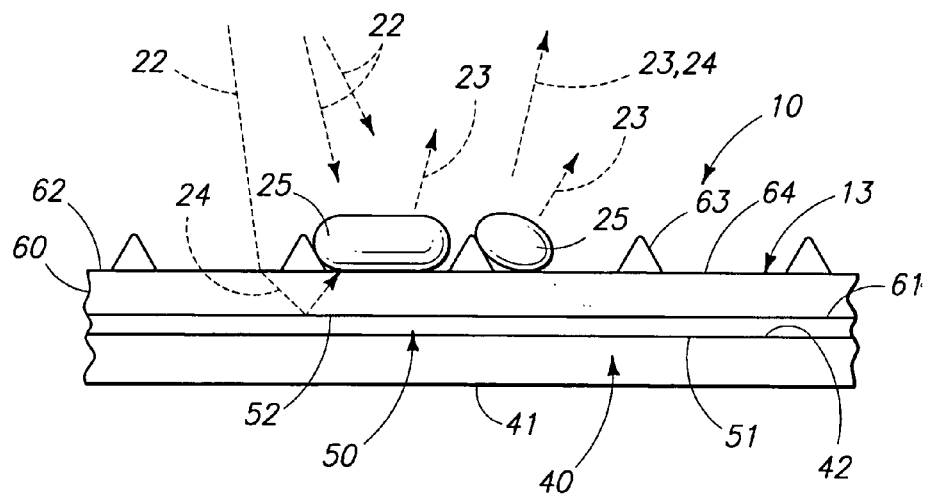
FIG. 2 is a greatly enlarged, transverse, vertical, sectional view of a portion of an endless belt for an object inspection system of the present invention.

Referring now to FIG. 2, it will be seen that the endless belt 10 of the present invention includes a flexible foundation layer which is generally indicated by the numeral 40. This flexible foundation layer can be made from a number of suitable substrates including synthetic and natural woven fabrics. For example, in one form of the invention, the foundation layer may comprise a fabric and a resin. The flexible foundation layer 40 has a first inside facing surface 41, and a second outwardly facing surface 42. The flexible foundation layer is typically opaque. Deposited in a suitable manner on the second outwardly facing surface 42 is a pigmented layer 50. The pigmented layer similarly has a first inside facing surface 51 which is juxtaposed relative to the second outwardly facing surface 42, and a second outwardly facing surface 52. The pigmented layer as depicted herein, when irradiated, reflects visible light which is perceived as the color blue. This background color provides contrast for the object to be inspected 25, and which rests upon the upper course 13 of the endless belt 10. However, other colors may be selected for the pigmented layer based upon the products to be inspected.

Referring still to FIG. 2, it will be seen that the endless belt includes a substantially transparent or transmissive layer 60 which is juxtaposed relative to the pigmented layer 50, and which supports the object to be inspected 25. In particular, the transparent or transmissive layer 60 has a first inwardly facing surface 61 juxtaposed relative to the second outwardly facing surface 52 of the pigmented layer and an opposite second outwardly facing surface 62. As seen in FIG. 2 and FIG. 4, the second outwardly facing surface 62 defines a plurality of spaced conically shaped projections or crowns 63 extending normally outwardly therefrom. Still further, a plurality of valley areas or regions 64 are defined between the respective conical projections 63 and wherein the object to be inspected 25 typically rests within these valley areas 64. The upwardly or outwardly facing surface 62 provides a coefficient of friction which inhibits or otherwise restrains the movement of the object to be inspected relative to the substantially transparent layer 60. Still further, the substantially transparent and transmissive layer 60 reflects, refracts and in some cases absorbs some bands or wavelengths of electromagnetic radiation in order to achieve the benefits of the present invention. For example, it should be understood that in some forms of the invention, the substantially transparent layer, depending upon its composition, may reflect 23, at least in part, only a portion of the electromagnetic radiation 22 which is emitted from the source of electromagnetic radiation 21. This may be due in part, to the absorption of a portion of the electromagnetic radiation by the transparent layer 60, pigmented layer 50, product 25 or all three. In another form of the invention, the electromagnetic radiation 22 may comprise visible light and wherein the substantially transparent 60 is substantially optically transparent and is operable to pass substantially all bands of the visible light substantially equally. In another possible form of the invention, the source of electromagnetic radiation 22 may provide a selected discrete band of wavelengths. For example, these wavelengths may comprise visible light, invisible electromagnetic radiation, or both. In one possible form of the invention, the second substantially transparent layer passes selected wavelengths in greater amounts than other wavelengths. This may be achieved by means of a dichroic film which is made integral with the transparent/transmissive layer 60 or a composition which is mixed with the transparent/transmissive layer 60 in order to achieve the desired dichroic effect. Still further, the transparent/transmissive layer 60 may comprise a polarizing filter film or an optical filter of film that is selected to pass only a portion of the electromagnetic radiation 22 which is directed toward same. As seen in FIG. 2, it will be understood that the transparent/transmissive layer 60 is operable to permit the passage of electromagnetic radiation 22 which is passed and reflected, in part, by the optically transparent layer 60 so as to substantially reduce any shadow created by the object 25 to be inspected as it rests upon the endless belt 10 and is transmitted along a course of travel provided by the endless belt.

OPERATION

The operation of the described embodiment of the present invention is believed to be readily apparent and is briefly summarized at this point.

An endless belt 10 for use in an object inspection system 20 includes, in its broadest respects, a flexible foundation layer 40; and a substantially transparent layer 60 juxtaposed upon the flexible foundation layer 40, and which supports an object to be inspected 25, and which reflects and refracts a source of electromagnetic radiation 22 so as to irradiate the object to be inspected.

More specifically, the present invention relates to an endless belt 10 for an object inspection system 20 which includes an opaque flexible foundation layer 40; and a contact layer 60 having a first side 61, and an opposite second side 62, and which is typically fabricated from a substantially transparent material, and wherein the first side 61 is juxtaposed relative to the flexible foundation layer 40, and wherein the contact layer 60 supports an object to be inspected 25. The present invention includes a source of electromagnetic radiation 21 which is positioned above, and is directed at the endless belt 10, and which is partly reflected 23 by the first side 61 of the contact layer, and partly refracted by the substantially transparent material 60, and partly reflected by the second side 62 of the contact layer so as to irradiate the object to be inspected 25. The second side 62 of the contact layer 60 has a surface topology 63 and 64 which creates a coefficient of friction, and which inhibits the movement of the object to be inspected 25 relative to the endless belt 10.

Therefore, it will be seen that the endless belt 10 for an object inspection system 20 as described herein provides a convenient means whereby an object to be inspected may be supported in an advantageous fashion so as to be irradiated and thereafter inspected in a fashion not possible heretofore.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An endless belt for an object inspection system, comprising:
    a flexible foundation layer; and
    a substantially transparent layer juxtaposed upon the flexible foundation layer, and which supports an object to be inspected, and which reflects and refracts a source of electromagnetic radiation so as to irradiate the object to be inspected; and a pigmented layer physically distinct from the flexible foundation layer and positioned between the flexible foundation layer and the substantially transparent layer, and wherein the pigmented layer reflects some wavelengths within the visible spectrum and absorbs other wavelengths within the visible spectrum.

2. The endless belt as claimed in claim 1, and wherein the source of elecromagnetic radiation comprises visible light, and wherein the substantially transparent layer is substantially optically transparent.

3. The endless belt as claimed in claim 1, and wherein the source of electromagnetic radiation comprises a discrete band of wavelengths.

4. The endless belt as claimed in claim 1, and wherein the source of electromagnetic radiation comprises a given band of wavelengths, and wherein the substantially transparent layer passes substantially all wavelengths within the given band of wavelengths in equal amounts.

5. The endless belt as claimed in claim 1, and wherein the source of electromagnetic radiation comprises a given band of wavelengths, and wherein the substantially transparent layer passes selective wavelengths in greater amounts than other wavelengths.

6. The endless belt as claimed in claim 1, and wherein the source of electromagnetic radiation comprises a given band of wavelengths, and wherein the pigmented layer reflects the given band of wavelengths in substantially equal amounts.

7. The endless belt as claimed in claim 1, and wherein the substantially transparent layer further defines a topography which provides a coefficient of friction which inhibits the movement of the object to be inspected relative to the substantially transparent layer.

8. An endless belt for an object inspection system, comprising:
    a flexible foundation layer;
    a contact layer having a first side, and an opposite second side, and which is fabricated from a substantially transparent material, and wherein the first side is juxtaposed relative to the flexible foundation layer, and wherein the contact layer supports an object to be inspected a pigmented layer physically distinct from the contact layer and positioned between the flexible foundation layer and the contact layer, and wherein the pigmented layer reflects some wavelengths within the visible spectrum and absorbs other wavelengths within the visible spectrum; and
    a source of electromagnetic radiation directed at the endless belt, which is partly reflected by the first side of the contact layer, and partly refracted by the substantially transparent material, and partly reflected by the second side of the contact layer so as to irradiate the object to be inspected; and wherein the second side of the contact layer has a surface topology which creates a coefficient of friction, and which inhibits the movement of the object to be inspected relative to the endless belt.

9. The endless belt as claimed in claim 8, and wherein the electromagnetic radiation has a wavelength that lies within the band of visible light, and wherein the contact layer is substantially optically transparent.

10. The endless belt as claimed in claim 8, and wherein the contact layer further comprises a dichroic layer.

11. The endless belt as claimed in claim 8, and wherein the contact layer further comprises a polarizing filter.

12. The endless belt as claimed in claim 8, and wherein the contact layer further comprises an optical filter that is selected to pass only a portion of the electromagnetic radiation.

13. An endless belt for an object inspection system, comprising:
    a first foundation layer fabricated from a fabric and a resin;
    a second pigmented layer juxtaposed relative to the first layer;
    a third substantially transparent contact layer with a first side, and an opposite second side, and wherein the first side of the third layer is juxtaposed relative to the second layer, and wherein the second side of the third layer supports an object to be inspected, and which further defines a plurality of crowns and valleys within which the object to be inspected is positioned, and which further provides a coefficient of friction which substantially inhibits the relative motion of the object to be inspected; wherein the second pigmented layer is positioned between the first foundation layer and the third substantially transparent contact layer, and wherein the second pigmented layer reflects some wavelengths within the visible spectrum and absorbs other wavelengths within the visible spectrum.

14. An endless belt for an object inspection system, comprising:
    an opaque flexible foundation layer having an upwardly facing surface;
    an optically transparent layer deposited upon the upwardly facing surface of the flexible foundation layer, and which supports an object to be inspected; a pigmented layer physically distinct from the flexible foundation layer and positioned between the flexible foundation layer and the optically transparent layer, and wherein the pigmented layer reflects some wavelengths within the visible spectrum and absorbs other wavelengths within the visible spectrum; and
    a source of electromagnetic radiation positioned above the endless belt, and which, when energized, emits electromagnetic radiation which is directed onto the endless belt and the object to be inspected, and wherein the emitted electromagnetic radiation is passed, and reflected in part, by the optically transparent layer so as to substantially reduce any shadow created by the object to be inspected on the endless belt.

* * * * *